United States Patent [19]

Canter et al.

[11] Patent Number: 4,872,838
[45] Date of Patent: Oct. 10, 1989

[54] ORAL INSPECTION DEVICE

[76] Inventors: Wade Canter; Kimberly Canter, both of 23675 Park Andorra, Calabasas Park, Calif. 91302; Shawn Canter; Chip Canter, both of 19274 Berclair La., Tarzana, Calif. 91356

[21] Appl. No.: 67,306

[22] Filed: Jun. 29, 1987

[51] Int. Cl.[4] ............................................. A61C 3/00
[52] U.S. Cl. .................................................. 433/31
[58] Field of Search ................... 433/30, 31; 128/11, 128/12, 22

[56] References Cited

U.S. PATENT DOCUMENTS

| | | | |
|---|---|---|---|
| 336,510 | 2/1886 | Criado | 128/11 |
| 1,079,414 | 11/1913 | Jirka | 433/30 |
| 1,201,550 | 10/1916 | Brush | 128/11 |
| 1,509,041 | 9/1924 | Hyams | 433/31 |
| 1,945,380 | 1/1934 | Russell | 128/11 |
| 2,125,980 | 8/1938 | Basil | 433/31 |
| 2,454,041 | 11/1948 | De Meo | 350/640 |
| 2,525,181 | 10/1950 | Ransdell | 433/30 |
| 4,212,105 | 7/1980 | Hukuba | 433/30 |

FOREIGN PATENT DOCUMENTS 0159690 3/1921 United Kingdom ................. 128/11

Primary Examiner—Gene Mancene
Assistant Examiner—Adriene J. Lepiane
Attorney, Agent, or Firm—Blakely, Sokoloff, Taylor & Zafman

[57] ABSTRACT

The present invention comprises an improved oral self inspection device that is versatile, inexpensive, and easy to use. The device consists of a small, cylindrical light source on which a small front primary or inspection mirror, a larger rear secondary or ocular mirror, and a cheek and tongue extender are mounted. Each of these implements is mounted at the end of an arm whose other end is rotatably and slideably mounted on the cylindrical light source. Each such arm is independently rotatable a full 360 degrees around the body of the cylindrical light source, such that the relative angular position between each of the implements is infinitely variable. Each of the arms is also independently slideable along the cylindrical light source, such that the relative separation between the implements can also be readily changed. The primary mirror may be attached to its mounting arm at a fixed angle, or the angle of tilt may be adjustable. The secondary mirror is mounted to its arm by means of a universal ball joint such that its angular orientation can be easily changed. The secondary mirror consists of a concave mirror on one side and a flat mirror on the other side to allow both magnified and unmagnified viewing of the image reflected by the primary mirror. The tongue and cheek extender consists of a resilient arm having a flat enlarged portion at one end which can be positioned adjacent the primary mirror such that it maintains a person's cheek or tongue to one side of the primary mirror and a clear line of sight from the secondary mirror to the primary mirror is maintained.

16 Claims, 1 Drawing Sheet

ORAL INSPECTION DEVICE

BACKGROUND OF THE INVENTION

1. Field of the Invention

The present invention relates to the field of oral inspection devices, and specifically to a hand-held, illuminated device for self-inspection of a person's mouth for cavities, cancer, or other oral diseases.

2. Prior Art

U.S. Pat. No. 4,212,105 discloses an inspection device for cavities comprising a small, tiltable primary inspection mirror mounted on an arm slideably attached to one end of a cylindrical light source, and a larger, concave, secondary mirror attached by means of a set of ball joints to a mounting arm fixedly attached to the other end of the cylindrical light source. The device is used by turning on the flashlight, placing the primary inspection mirror in one's mouth, and viewing the primary mirror by means of the secondary mirror. An actuating means allows the tilt of the primary inspection mirror with respect to its mounting arm to be adjusted to adjust the angle of view. The ball joints on which the secondary mirror is mounted allow adjustment of the orientation of the secondary mirror as well as a limited amount of adjustment of the separation between the primary and the secondary mirrors.

Although this device works satisfactorily for some individuals, for others it has proven to be awkward or difficult to use. One problem with the device is the limited extent of the adjustability of the distance between the two mirrors. For persons with normal vision, such limited adjustment does not cause any problem. For persons who are nearsighted or farsighted, however, such limited adjustment can prevent such individuals from being able to focus on the image being reflected by the mirrors. This is particularly the case when the secondary mirror, as used in the prior art device, is a concave, magnifying mirror. Another problem that arises with the use of the prior art device is that when the device is used to inspect the sides or the back of the mouth, the cheeks or tongue of the individual may interfere with the line of sight between the secondary and primary mirrors. To be able to view such areas of the mouth, it is necessary for the user to push the cheek or the tongue out of the way using an implement such as a tongue depressor or a finger. Two hands are therefore needed to use the device in such circumstances: one to hold the inspection device itself, and the other to move the tongue or cheek out of the way. Such use of two hands is awkward and uncomfortable. To adjust the mirrors and hold the device and simultaneously to use your other hand to deflect the cheek or tongue to have a clear field of vision as required by the prior art is impossible for older, handicapped or people that are not extremely dexterous. Many older people may require two hands to hold the device steady and thus couldn't use the prior art. Not only does the new art with the tongue and check deflector built in allow easy use by older, non-dexterous and handicapped people, but the new art also allows a person to use the device and use the other hand to remove impacted debris caught between teeth and to dry off areas such as a possible oral cancer for better viewing. This is particularly important when doing an oral pathology and oral cancer self examination because you have to hold the tongue and manipulate the mirror with one hand to see lateral and posterior areas and you need the cheek retracted or deflected at the same time. Also, for anybody who has a gagging problem, it is almost impossible to use your finger to reflect the cheek or tongue. Again in using an oral cleaning device such as a Prox-a-brush, periodontal aid, stimulator, etc., you need one hand to hold the instrument while the new art allows you to see and retract or deflect the cheeks and tongue for visability. When using orthodontic elastics with one hand, you need the new art to retract the cheek and tongue for visability and access. To put on topical medication you need new art to retract or deflect cheek and tongue to allow acess and visability.

BRIEF SUMMARY OF THE INVENTION

The present invention comprises an improved oral self inspection device that is versatile, inexpensive, and easy to use. The device consists of a small, cylindrical light source on which a small front primary or inspection mirror, a larger rear secondary or ocular mirror, and a cheek and tongue deflector are mounted. Each of these implements is mounted at the end of an arm whose other end is rotatably and slideably mounted on the cylindrical light source. Each such arm is independently rotatable a full 360 degrees around the body of the cylindrical light source, such that the relative angular position between each of the implements is infinitely variable. Each of the arms is also independently slideable along the cylindrical light source, such that the relative separation between the implements can also be readily changed. The primary mirror may be attached to its mounting arm at a fixed angle, or the angle of tilt may be adjustable. The secondary mirror is mounted to its arm by means of a universal ball joint such that its angular orientation can be easily changed. The secondary mirror consists of a concave mirror on one side and a flat mirror on the other side to allow both magnified and unmagnified viewing of the image reflected by the primary mirror. The tongue and cheek deflector consists of a resilient arm having a flat enlarged portion at one end which can be positioned adjacent the primary mirror such that it maintains a person's cheek or tongue to one side of the primary mirror and a clear line of sight from the secondary mirror to the primary mirror is maintained.

DETAILED DESCRIPTION OF THE INVENTION

An improved oral self inspection device is disclosed. In the following description, for purposes of explanation, numerous details are set forth, such as specific materials, arrangements and proportions in order to provide a thorough understanding of the present invention. However, it will be apparent to one skilled in the art that the invention may be practiced without these specific details. In other instances, well known articles, such as penlights, ball joints, and mirrors have not been described in detail in order not to obscure the present invention unnecessarily.

Figure 1:
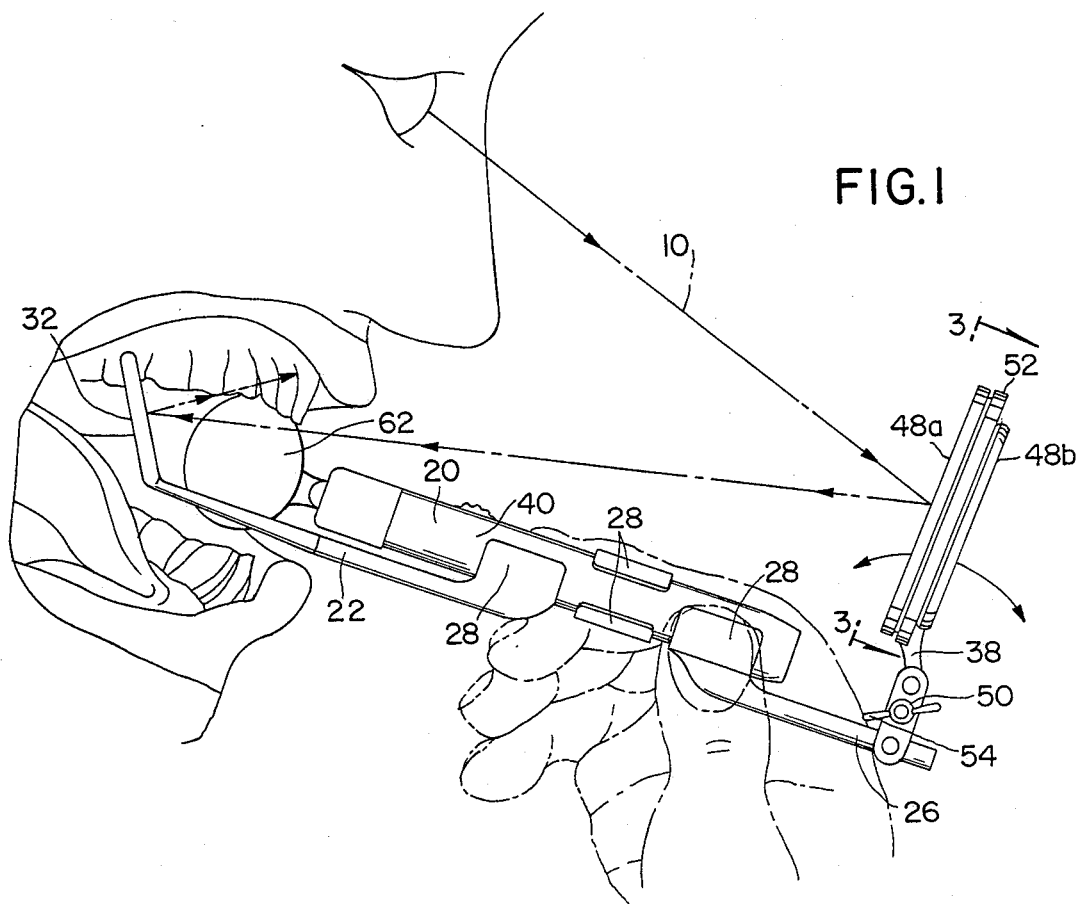
FIG. 1 is a side view of one embodiment of the present device, illustrating how the device can be used for oral self inspection.
Figure 2:
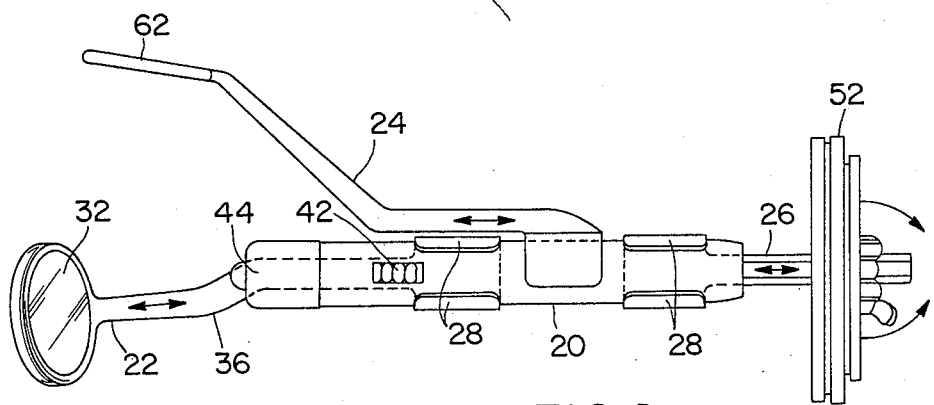
FIG. 2 is a top view of the embodiment of FIG. 1.

Referring first to FIGS. 1 and 2, the present invention comprises a small, elongated light source 20, such as a penlight, on which a plurality of implement carrying arms 22, 24, and 26 are slideably and rotatably mounted. In the preferred embodiment, light source 20 is a penlight having an elongated, cylindrical housing 40 of essentially constant cross sectional area, a bulb 44 at its front end, and an on/off switch 42. Each of the implement carrying arms 22, 24 and 26 comprise a first mounting means at a first end for mounting of said arm to cylindrical light source 20 and a second mounting means at a second end for mounting oral inspection and cleaning implements such as mirrors, scrapers, polishers, and tongue and cheek guards.

In the preferred embodiment, the first mounting means for mounting the arms to the light source 20 comprise a pair of semicylindrical tabs 28 shaped so as to snugly fit around light source 20. The tabs are preferably made of a flexible material such that they may be elastically deformed such that the arms may easily be snapped on or off the cylindrical housing of light source 20. Tabs 28 should fit tightly enough around light source 20 such that the frictional force between tabs 28 and light source 20 will normally maintain the arm in a set position during use. However, the tabs should fit loosely enough to allow the arms to be rotated around the cylindrical housing of light source 22 or slid back and forth without any undue effort. Tabs 28 are preferably integrally formed with the rest of arms 22, 24, or 26.

In the embodiment of FIG. 1, implement carrying arms 22, 24 and 26 comprise a primary inspection holding arm 22, a cheek extender arm 24, and a secondary mirror mounting arm 26.

Primary mirror mounting arm 22, as shown in FIGS. 1 and 2, comprises an elongated, substantially straight arm, with a small, round, primary mirror 32 mounted at its foremost end. Primary mirror 32 may be mounted to primary mirror holding arm 22 at a fixed angle, as in the embodiment of FIGS. 1 and 2, or primary mirror 32 may be attached to primary mirror mounting arm 22 by a hinge or ball joint such that the orientation of mirror 32 is adjustable. As illustrated in FIG. 2, primary mounting arm 22 may contain an offset 36 such that primary mirror 32 is offset a limited amount from the longitudinal central axis of light source 20 to prevent any obstruction of the line of sight between primary mirror 32 and secondary mirror 52.

Figure 3:
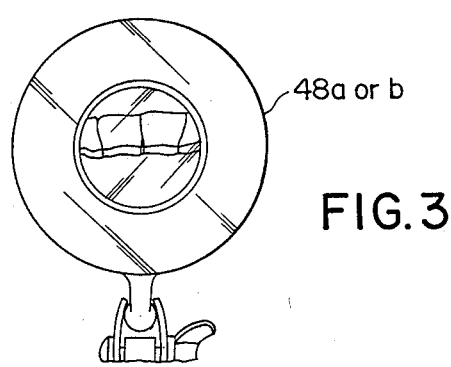
FIG. 3 is a front view of the secondary mirror of the embodiment of FIG. 1, illustrating the image seen by a person using the device as illustrated in FIG. 1.

Secondary mirror mounting arm 26 comprises an elongated arm generally shorter than primary mirror mounting arm 22 at the rear most end of which is mounted secondary mirror assembly 52. Secondary mirror assembly 52 comprises an adjustable universal ball joint 50, a mirror mounting platform 38 attached to universal ball joint 50, and mirrors 48a and 48b mounted on either side of mounting platform 38. Universal ball joint 50 allows mirror mounting platform 38 to be fully adjustable in orientation around two axes. In the preferred embodiment, universal joint 50 may be tightened or loosened by adjusting wing nut 54. Mirrors 48a and 48b are preferably larger than primary mirror 32, and are also preferably round. In the preferred embodiment, mirror 48a is a concave, magnifying mirror, while mirror 48b is a flat, plane mirror In use, as shown in FIG. 1, secondary mirror assembly 52 is adjusted such that the image of the inside of the mouth is reflected off primary mirror 32 and secondary mirror 48a or 48b to the eyes of the user, as indicated by path 60 in FIG. 1. If magnifying mirror 48a is used, the distance between primary mirror 32 and secondary mirror 48a may have to be adjusted for the magnified image to be properly in focus for the user. Where the detailed view provided by magnifying mirror 48a is not required, the flat mirror 48b can be used to eliminate the need for focusing. The light projected by light source 20 is reflected off primary mirror 32 to illuminate the site being inspected. A typical view of the image reflected in secondary mirror 48a or 48b during use of the present invention is illustrated in FIG. 3.

Tongue and cheek extender 24 comprises a bent, semirigid, flat, elongated arm that extends outwards and forwards from light source housing 20. In the preferred embodiment, tongue and cheek extender 24 features an enlarged, circular flat front end 62. Tongue and cheek extender 24 is used to prevent a person's cheek and/or tongue from interfering with the line of sight between the secondary and primary mirrors. In prior art devices, the cheek and/or tongue often interfered with inspection of the remoter areas of the mouth. Inspection of such areas is important because there are areas in which oral cancer may develop. With the tongue and cheek extender of the present invention, however, inspection of the entire mouth cavity, including these areas, is possible. Like primary mirror mounting arm 22 and secondary mirror mounting arm 26, tongue/cheek extender 24 can be easily adjusted for angular orientation and lateral position.

In the preferred embodiment, primary mounting arm 22, tongue/cheek extender 24 and secondary mirror mounting arm 26 are preferably formed of a plastic material, although a metal or other material may also be used.

Accordingly, a novel oral self inspection device has been presented. The present invention provides a combination of versatility and ease of use that was not available in the prior art. Although specific details are described herein, it will be understood that various changes can be made in the materials, details, arrangements and proportions of the various elements of the present invention without departing from the scope of the invention. For example, although the specification refers primarily to the use of round primary and secondary mirrors, mirrors of other shapes can be used. The mounting arms of the present invention need not have the specific design or configuration illustrated in the drawings. For instance, the arms may be longer or shorter, and may be mounted in any order or combination on the body of light source 20. In addition to primary mirror 32, other oral hygiene implements may be affixed to light source 20. For instance, primary mirror 32 may be replaced with a variety of teeth cleaning and polishing implements. Other variations will be apparent to those skilled in the art.

I claim:

1. An oral inspection device for allowing self-inspection of a person's oral cavity, comprising:
   an elongated body having a longitudinal axis suited for gripping by said person's hand and containing illuminating means at a first end thereof;
   at least three elongated support means each having a first end detachably mounted on a said elongated body and a second end for supporting oral inspection and cleaning means wherein each of said support means are free to slideably move along said elongated body substantially parallel to said longitudinal axis and rotate about said longitudinal axis;

a first of said elongated support means extending laterally and longitudinally away from said first end of said elongated body, said first elongated support supporting first oral inspection and cleaning means comprising means for biasing a person's cheek and tongue away from said longitudinal axis of said elongated body such that said illuminating means can provide unobstructed illumination of said person's oral cavity;

a second of said elongated support means extending longitudinally away from said first end of said elongated body for supporting a second oral inspection and cleaning means within said person's oral cavity while a portion of said elongated body remains without said oral cavity, said second oral inspection and cleaning means including a primary mirror for receiving an image of a portion of the person's oral cavity which is being observed, and reflecting said image; and, a third of said elongated support means extending from a second end of said elongated body, said third elongated support means supporting a secondary mirror means for receiving said reflected image from said primary mirror and re-directing that image to the person's eye for viewing of said portion of the person's oral cavity during the operation of said device.

2. The oral inspection device of claim 1 wherein said primary mirror is fixedly mounted to said second end of said second elongated support means.

3. The oral inspection device of claim 1 wherein said primary mirror is moveably mounted to said second end of said second elongated support means such that the orientation of said primary mirror with respect to said second elongated support means is freely adjustable.

4. The oral inspection device of claim 1 wherein said first end of each of said at least three elongated support means comprises sleeve means slideably and rotatably engageable on said elongated body.

5. The oral inspection device of claim 4 wherein said sleeve means comprises a longitudinal slot allowing said elongated support means to be mounted and removed along a radial direction perpendicular to said longitudinal axis of said elongated body.

6. The oral inspection device of claim 1 wherein said secondary mirror means includes ocular mirror means moveably mounted to said second end of said third elongated support means such that the orientation of said ocular mirror means with respect to said third elongated support means is adjustable.

7. The oral inspection device of claim 6 wherein said ocular mirror means is mounted to said second end of said third elongated support means by means of a ball joint means.

8. The oral inspection device of claim 6 wherein said ocular mirror means comprises a concave mirror which magnifies any images received from said primary mirror.

9. The oral inspection device of claim 6 wherein said ocular mirror means comprises a planar mirror.

10. The oral inspection device of claim 6 wherein said ocular mirror means comprises a planar mirror on a first side of said ocular mirror means and a concave mirror on a second side of said ocular mirror means, said ocular mirror means being rotatable between a first position in which said planar mirror receives said images from said second oral inspection and cleaning means and a second position in which said concave mirror receives said images from said second oral inspection and cleaning means.

11. The oral inspection device of claim 10 wherein said second oral inspection and cleaning means comprises an inspection mirror means.

12. An oral inspection device for allowing self-inspection of a person's oral cavity comprising:

an elongated body having a longitudinal axis suited for grasping by a human hand and containing illuminating means at a first end thereof;

at least three elongated support means each having a first end detachably mounted on said elongated body and a second end for supporting oral inspection and cleaning means wherein each of said support means is free to slideably move along said elongated body substantially parallel to said longitudinal axis and rotate about said longitudinal axis, said first end of each of said elongated support means comprises sleeve means including a longitudinal slot allowing said elongated support means to be mounted and removed along a radial direction perpendicular to said longitudinal axis of said elongated body;

a first of said elongated support means extending longitudinally away from said first end of said elongated body for supporting an inspection mirror means within a person's oral cavity;

a second of said elongated support means extending from a second end of said elongated body, said second elongated support means supporting an ocular mirror means for receiving images from said inspection mirror means, said ocular mirror means comprising a planar mirror on a first side of said ocular mirror means and a concave mirror on a second side of said ocular mirror means, said ocular mirror means being rotatable between a first position in which said planar mirror receives said images from said inspection mirror means and a second position in which said concave mirror receives said images from said inspection mirror means, said ocular mirror means for re-directing said images from the inspection mirror to the person's eye for viewing that portion of the person's oral cavity during the operation of said device; and, a third of said elongated support means extending laterally and longitudinally away from said first end of said elongated body and supporting means for biasing a said person's cheek and tongue away from said longitudinal axis of said elongated body and from said inspection mirror means such that said ocular mirror means receives an obstructed view of said inspection mirror means.

13. The oral inspection device of claim 12 wherein said elongated body comprises a penlight.

14. The oral inspection device of claim 12 wherein said first end of each of said at least three elongated support means comprises sleeve means slideably and rotatably engageable on said elongated body.

15. The oral inspection device of claim 12 wherein said elongated support means are comprised primarily of a plastic material.

16. The oral inspection device of claim 12 wherein said elongated support means are comprised primarily of a metal.

* * * * *

UNITED STATES PATENT AND TRADEMARK OFFICE
CERTIFICATE OF CORRECTION

PATENT NO. : 4,872,838
DATED : October 10, 1989
INVENTOR(S) : Canter et al

It is certified that error appears in the above-indentified patent and that said Letters Patent is hereby corrected as shown below:

Column 3, line 63, after "mirror" insert —.—.

Signed and Sealed this

Twelfth Day of July, 1994

Attest:

BRUCE LEHMAN

Attesting Officer          Commissioner of Patents and Trademarks